US009784852B1

(12) United States Patent
Majewski et al.

(10) Patent No.: US 9,784,852 B1
(45) Date of Patent: Oct. 10, 2017

(54) SURGICAL GUIDANCE SYSTEM USING HAND-HELD PROBE WITH ACCOMPANYING POSITRON COINCIDENCE DETECTOR

(75) Inventors: Stanislaw Majewski, Yorktown, VA (US); Andrew G. Weisenberger, Yorktown, VA (US)

(73) Assignee: JEFFERSON SCIENCE ASSOCIATES, LLC, Newport News, VA (US)

( * ) Notice: Subject to any disclaimer, the term of this patent is extended or adjusted under 35 U.S.C. 154(b) by 1632 days.

(21) Appl. No.: 11/707,579

(22) Filed: Feb. 16, 2007

(51) Int. Cl.
*A61B 6/00* (2006.01)
*G01T 1/20* (2006.01)
*G01T 1/161* (2006.01)
*G01T 1/16* (2006.01)
*A61N 5/10* (2006.01)

(52) U.S. Cl.
CPC .......... *G01T 1/2008* (2013.01); *A61B 6/4208* (2013.01); *A61B 6/4258* (2013.01); *A61B 6/4266* (2013.01); *A61B 6/4405* (2013.01); *A61N 5/103* (2013.01); *G01T 1/161* (2013.01); *G01T 1/1603* (2013.01)

(58) Field of Classification Search
CPC . B61K 9/04; G01J 5/041; G01J 5/0022; G01J 5/048; G01J 5/0809; A61B 6/428; A61B 6/4258; A61B 6/4266; A61B 6/4405; A61N 5/103; G01T 1/1603; G01T 1/161; G01T 1/2008
USPC .......................................................... 600/436
See application file for complete search history.

(56) References Cited

U.S. PATENT DOCUMENTS

| 5,866,907 | A | * | 2/1999 | Drukier et al. ............... 250/366 |
| 6,643,538 | B1 | * | 11/2003 | Majewski et al. ............ 600/436 |
| 7,612,342 | B1 | * | 11/2009 | Nagarkar ..................... 250/362 |
| 2004/0015075 | A1 | * | 1/2004 | Kimchy et al. ............... 600/424 |
| 2006/0054863 | A1 | * | 3/2006 | Dai et al. ............... 252/301.4 R |
| 2007/0045564 | A1 | * | 3/2007 | Fu .............................. 250/483.1 |

OTHER PUBLICATIONS

Farsoni,Simultaneous Beta/Gamma Digital Spectroscopy , Dec. 2006.*

* cited by examiner

*Primary Examiner* — Ruth S Smith

(57) ABSTRACT

A surgical guidance system offering different levels of imaging capability while maintaining the same hand-held convenient small size of light-weight intra-operative probes. The surgical guidance system includes a second detector, typically an imager, located behind the area of surgical interest to form a coincidence guidance system with the hand-held probe. This approach is focused on the detection of positron emitting biomarkers with gamma rays accompanying positron emissions from the radiolabeled nuclei.

4 Claims, 6 Drawing Sheets

SURGICAL GUIDANCE SYSTEM USING HAND-HELD PROBE WITH ACCOMPANYING POSITRON COINCIDENCE DETECTOR

The United States of America may have certain rights to this invention under Management and Operating Contract DE-AC05-06OR23177 from the United States Department of Energy.

FIELD OF THE INVENTION

The present invention relates to surgical guidance systems and more particularly to such a system using a hand-held probe in combination with an accompanying positron coincidence detector.

BACKGROUND OF THE INVENTION

To assist with surgical removal of cancerous lesions, surgeons use hand-held guiding instruments such as intra-operative probes. Before surgery, patients are injected with radio-labeled biomarker which is predominantly uptaken by the cancer tissue.

Usually these devices are simple and work on the "Geiger counter" principle i.e. they only measure intensity of the radioactive signal in the vicinity of the probe sensor/tip and provide audio and/or visual feedback to the operator/surgeon (see for example, Ramsey et al., U.S. Pat. No. 4,889,991, Dec. 26, 1989, Denen et al., U.S. Pat. No. 5,151,598, Sep. 29, 1992, and Yarnall et al., U.S. Pat. No. 6,331,703, Dec. 18, 2001). By scanning the probe in front of the tissue and zooming on the region producing the strongest signal, the information on the lesion location is obtained, directly correlated with the anatomical detail, as visually analyzed by the surgeon. This time-consuming procedure suffers generally from poor probe sensitivity and, therefore, poor cancer margin definition.

There have been many attempts to address the issue of providing better, faster and more accurate cancer tissue position information by constructing small imaging probes. These mini-imagers can be for gamma imaging or for positron imaging, or for both. Several companies are producing such probes (for example, Gamma Medica and IntraMedical Imaging and many more designs are described in scientific literature and in patents such as U.S. Pat. No. 6,628,984 by Weinberg, Sep. 30, 2003.

However, all these instruments suffer from a major inconvenience from the surgeon's point of view which is that they locally obstruct the view of the surgical field and do not actually help with the exact location of the tissue to be surgically removed. More accurate and larger image of the scanned region per se but without optical etc co-registration with anatomical detail is deemed not to be that useful by surgeons.

In addition, these mini-imagers are not actually easily "hand-held" because their weight is usually in the range of 1-3 pounds. While mechanical support systems were designed to support the imaging probes in place, these devices further exacerbate the above mentioned viewing field obstruction issue. To remedy the obstruction and weight issues some of the proposed imaging probes are made compact with even smaller field of view, however then their utility as imagers is limited. Another approach is to limit the size of the instrument at the surgical end by installing thereon only a scintillator gamma sensor which is optically connected to a distant position sensitive photodetector via a flexible optical fiberoptic lightguide (Daghighian et al., U.S. Pat. No. 5,325,855, Jul. 5, 1994). However, in this case there are the same issues of visual field obstruction and limited field of view. Flexible light guides usually limit the field of view even more.

OBJECTS OF THE INVENTION

It is therefore an object of the present invention to provide a surgical guidance system that provides the greatest detailed view of the area of concern to the surgeon without the limitation of the visual field prevalent in prior art systems.

It is another object of the present invention to provide a surgical guidance system that is small and light enough to allow the surgeon to easily manipulate it without the need for visually impairing support systems.

SUMMARY OF THE INVENTION

In the system of the present invention, the imaging scan is of a larger surgical field, and thus providing much more accurate guidance in cancer removal. These benefits are obtained by the use of a device offering different levels of imaging capability while maintaining the same hand-held convenient small size of light-weight intra-operative probes. This is achieved by adding a second detector, typically an imager, located below or behind the patient or the area being surgically addressed to form a coincidence guidance system with the hand-held probe. This approach is focused on detection of positron emitting biomarkers with two 511 keV gamma rays accompanying positron emissions from the radiolabel nuclei.

DETAILED DESCRIPTION

Figure 1:
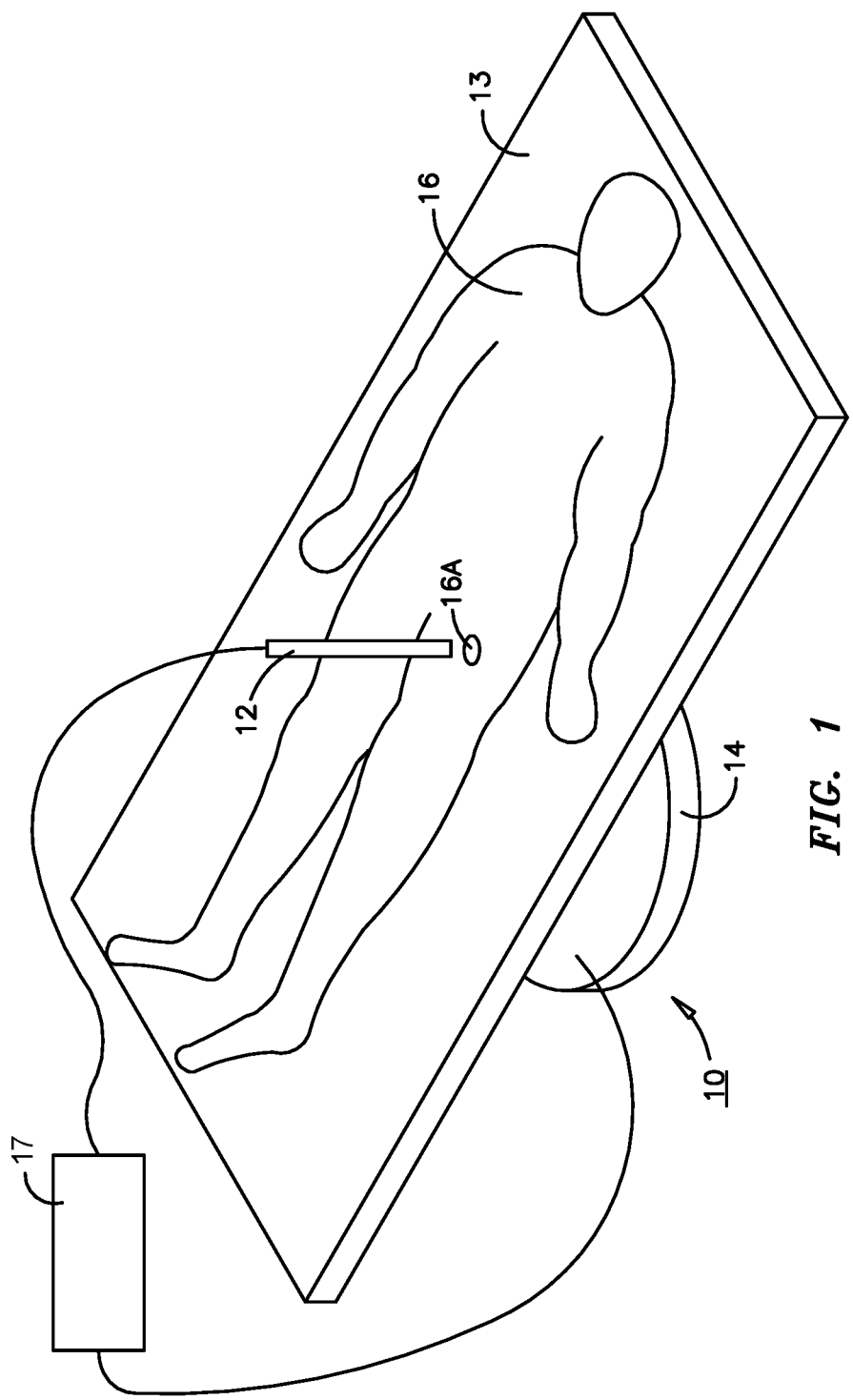
FIG. 1 is a schematic perspective view of the surgical guidance system of the present invention.
Figure 2:
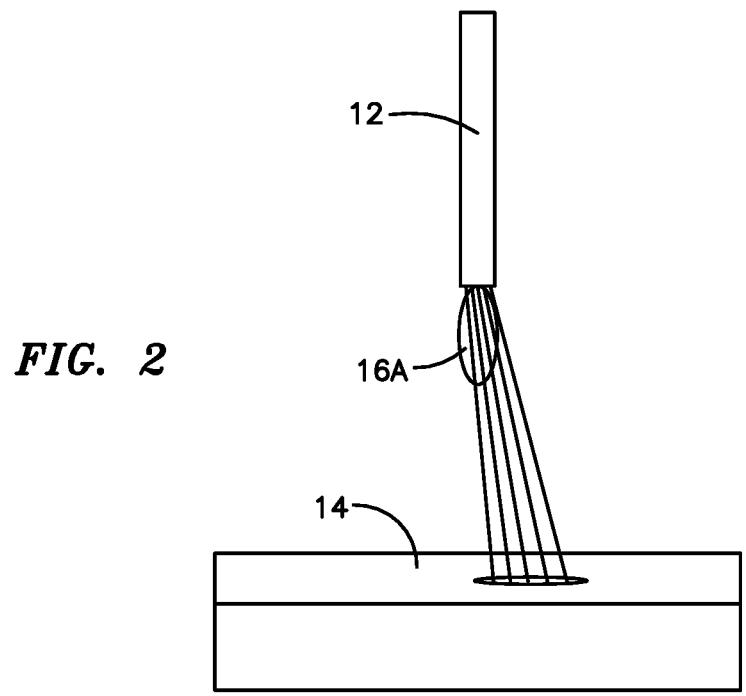
FIG. 2 is a schematic graphic representation of the use of the surgical guidance system of the present invention.

Referring now to accompanying FIGS. 1 and 2, the positron surgical guidance system 10 of the present invention is composed of three major components: 1) a compact hand-held detection probe 12 manipulated by the operator; 2) a coincidence imager 14 operating in conjunction with hand-held probe 12 and placed on the opposite side of the area being surgically addressed from probe 12, i.e. behind the organ, or body of the patient 16A and 16 respectively; and a set of fast hardware processors and software algorithms 17 providing immediate on the spot feedback to the operator/surgeon after analyzing multi-parametrical information received from the probe and coincident detector/imager.

Figure 3:
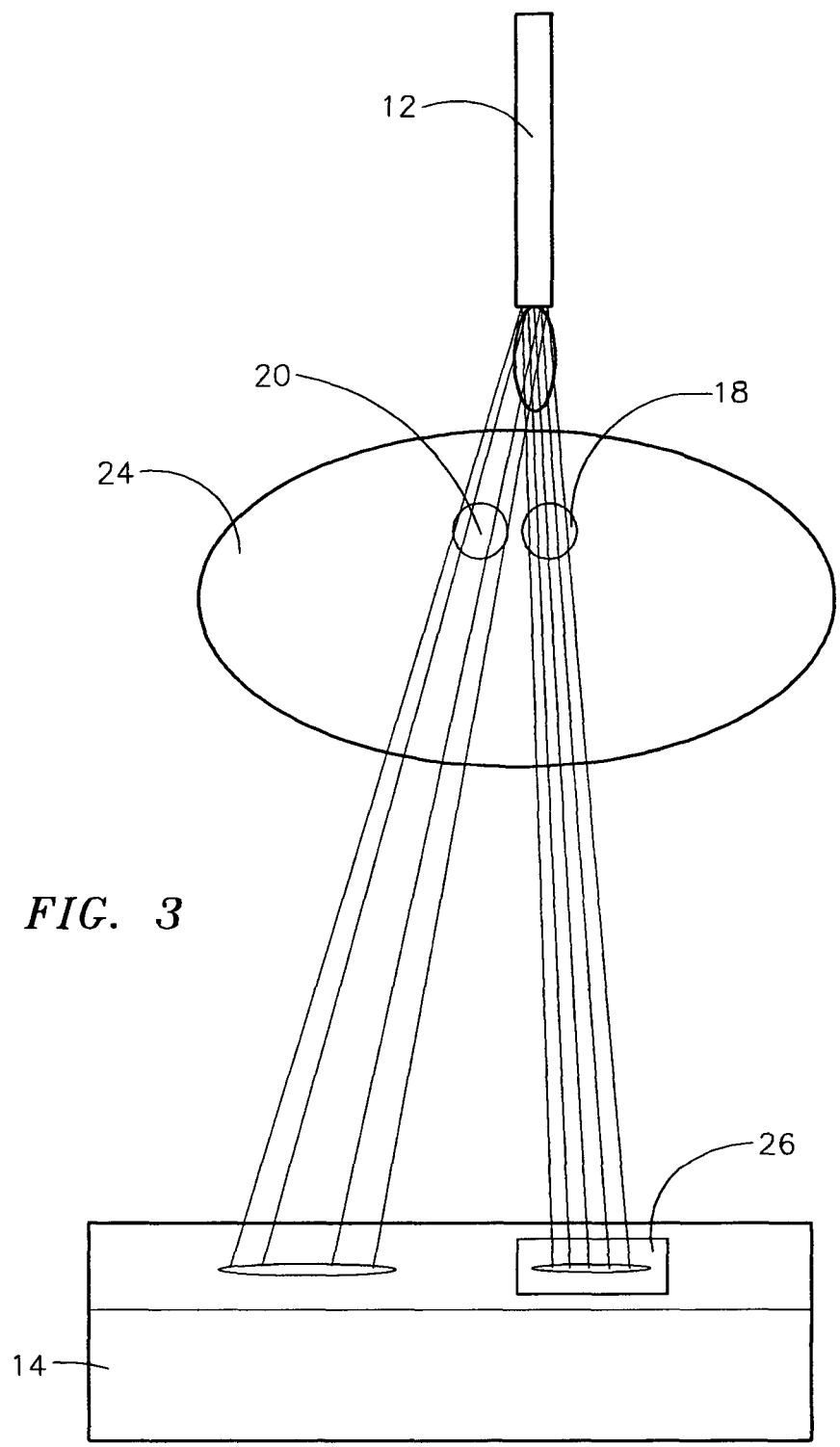
FIG. 3 represents a demonstration of the spot guiding principle using the surgical guidance system of the present invention.

In the case of several hot spots 18, 20 and 22 (see FIGS. 3 and 4) or an extended uptake field 24, adding a coincidence requirement with a corresponding region in the imaging coincidence detector system 14 and 12 will guide the probe to that particular hot spot or region, such as hot spot 18, without interference from the neighboring hot spots 20 and 22. During the operation of a standard prior art intraoperative probe with no accompanying imaging detector, this interference and signal overlap is unavoidable and even if some collimating schemes are considered, the efficiency of such a simple approach cannot match the advantages of the coincident system of the present invention. As depicted in FIG. 3, a spot selection condition 26 dependent upon the 20 "aim point" of hand-held probe 12 is defined such that coincidence imaging of primary "lesion" or spot 18 is obtained while secondary spot 20 is not coincidentally imaged by both hand-held probe 12 and coincidence imager 14.

In the surgical guidance system of the present invention 10, the geometry of a small size probe sensor 12 and a large imaging detector 14 on the opposite side of the organ 16A or patient body 16, sensitivity of the system (defined by number of coincidences) decreases quickly with distance from the probe sensor. This effect limits substantially the signal due to radiation background from radiation distributed in tissue behind the cancer tissue.

Figure 4:
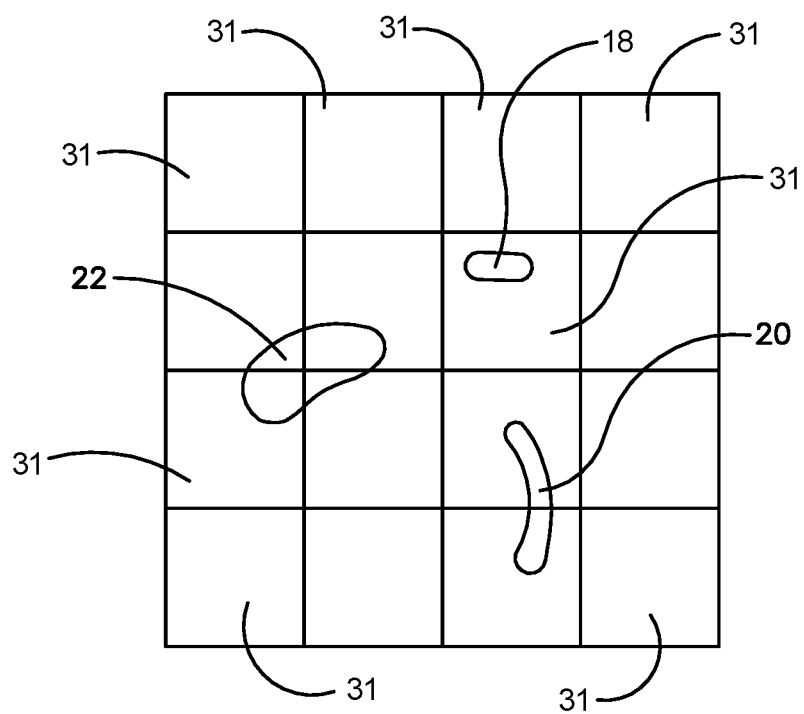
FIG. 4 is a graphic representation of the image generated by a modular coincidence detector in accordance with the present invention.

In the example represented in FIGS. 3 and 4, a spot guiding principle is demonstrated where a coincidence requirement between probe 12 and the selected region in the imager projection 26 helps in picking up signal from one of the neighboring spots, e.g. 18, while the second spot 22 is also seen in a more distant part of the coincidence imager. After removing (or biopsing) the first spot 18, the coincidence condition can be changed to focus on and guide the probe to second spot 22.

As depicted in FIG. 4, while not providing detailed images of the radiation distribution in tissue, surgical guidance system 10 can assist with differentiating between neighboring structures for better guidance to the hot spots or regions 18, 20 and 22. Coincident signal pattern can involve single or multiple detector 20 segments/tiles 31.

Figure 5:
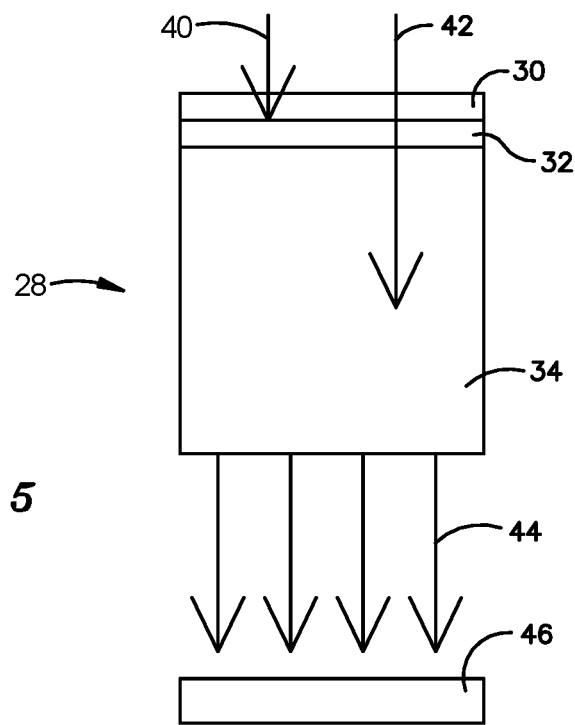
FIG. 5 is a schematic representation of a three-element beta/gamma sensor made from three scintillation materials in optical contact in accordance with one preferred embodiment of the present invention.

As described more fully below and depicted schematically in FIGS. 4 and 5, hand-held probe 12 can have different structures, with different levels of complexity and functionality. The basic design is composed of a single gamma radiation sensor (external size limits are from −1 mm3 to −10000 mm3 in volume). Typically, to keep balance between sensitivity and size of probe 12, the sensor will be a scintillator crystal on the order of a 5×5×15 mm$^3$. The primary role of the radiation sensor will be detecting 511 keV annihilation gamma rays, independently and in coincidence with the coincidence imager.

Figure 6:
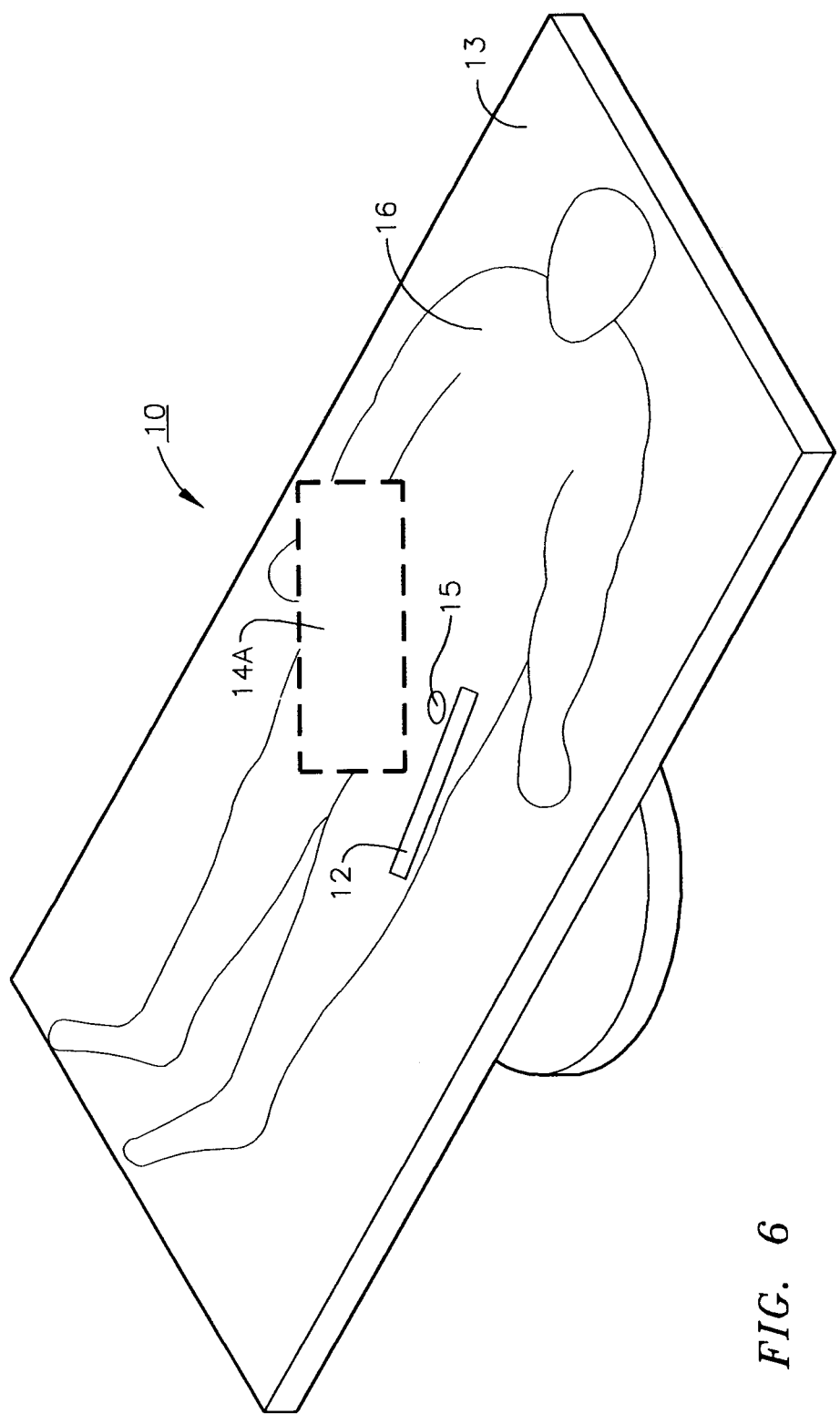
FIG. 6 is a schematic representation of a prostate imaging variant of the surgical guidance system of the present invention.

Coincidence imager 14, can be of differing sizes, varying from about 1 cm$^2$ to a 1 m$^2$ size. In special cases, it can be also a non-imaging type and usually larger than probe detector that operates in coincidence with the probe, and is placed on the opposite side of the organ, extremity or patient torso 16 as shown in FIGS. 1 and 6. As an intermediate option, the coincidence detector 14 can produce images of separate sectors with their coincidence signals (with probe 12) constantly analyzed to define radiation pattern and provide guidance to the operator/surgeon.

Coincidence detector 14 may comprise any of a long list of conventional materials including: solid state material, such as CdZnTe, CdTe, Si, etc.; scintillator materials such as high stopping power crystal scintillators (BGO, LSO, LYSO, GSO, LGSO, etc.) other inorganic scintillators such as NaI(Tl), CsI(Tl), CsI(Na), LaBr3, etc.; scintillating glasses; hybrid heavy converters (lead, tungsten, etc) with a gaseous electron amplification medium; hybrid with heavy converters (lead, tungsten, etc) with a plastic scintillator; hybrid with heavy converter (lead, tungsten, etc) and a liquid scintillator; hybrid with heavy converter (lead, tungsten, etc) and a high pressure gas scintillator; and liquid xenon or mixtures of xenon with krypton and other additives.

The active gamma sensitive element of the coincidence detector can be either a continuous material, forexample a plate of NaI(Tl) scintillator, or pixellated for example, an array of BGO pixels.

Probe 12 can be provided with increased functionally to detect betas (positrons) and gammas to enhance its positron detection capabilities (as described by Yamamoto et al., Annals of Nuclear Medicine Vol. 19, No. 1, 23-28, 2005). Two or even three types of materials can be used in such a dual-mode probe. The role of a thin entry detection element is to directly detect positrons (beta particles) emitted from radiolabel used in the applied biomarker. The beta detection element can be composed of a single layer or can be a set of two consecutive layers, operating in coincidence. In the latter case the beta sensor is highly selective for beta particles, a fraction of which will traverse the first layer and deposit another energy signal in the second layer. Gamma interactions will not produce simultaneous (coincident) signals from these two layers for the same events. By this signal differentiation, beta signals can be separated from the gamma background signals.

An example of a practical and preferred three element beta/gamma sensor is: 0.25 mm thick plastic scintillator (element 32 in FIG. 5) and 0.5 mm CaF(Eu) scintillator (element 30 in FIG. 5) for positrons, and 15 mm thick BGO scintillator (element 34 in FIG. 5) for 511 keV gammas. FIG. 5 depicts an example of a three-element beta/gamma sensor, probe 28 made of three scintillation materials in optical contact. Beta and gamma radiations 40 and 42 respectively enter sensor 28, beta radiation 40 is detected by beta sensitive layers 30 and 32, gamma radiation 42 is detected by gamma sensitive scintillator 34. Scintillation light 44 from all elements of this phoswich reaches the same photodetector 46 placed behind the gamma detecting sensor. The beta (positron) signals 40 require simultaneous scintillation from both two thin entry layers 30 and 32. The gamma sensor 34 is thick enough to have sufficient stopping power for 511 keV annihilation gamma rays. The three optically mixed scintillation signals are separated on the basis of their different time decay and amplitude characteristics.

Positron (beta) only probes have also been devised (for example those described by Raylman et al., U.S. Pat. No. 6,456,869. Sep. 24, 2002) to avoid signal interference from scattered gamma background, but their sensitivity is limited to only very shallow (<2-5 mm) tissue layers due to limited range of positrons in tissue. Therefore, while providing a clear signal from the exposed cancer tissue (providing that positron labeled biomarker is uptaken by the lesion/cancer) the beta only probe cannot detect emissions from deeper layers.

Compact hand-held gamma probes with directional guidance were designed (f.e. Majewski et al., U.S. Pat. No. 6,643,538, Nov. 4, 2003) but their guidance capability is limited to lower energy gamma rays (~140 keV) and positrons, i.e. they do not provide good directional guidance in detecting higher energy 511 keV gamma rays from the positron decays.

In the case of multilayer beta/gamma sensors comprising scintillation materials, the materials are preferably selected to have different pulse shapes so that a single photodetector can be used and the beta and gamma contributions are separated on the basis of this pulse shape. This so-called phoswitch structure can be built of a large variety of materials. Two simple examples are thin plastic scintillators or YAP crystal scintillators as used as beta sensors and optically attached to a gamma sensor such as GSO.

At another level of functionality, the probe sensors can be built from an array of sub-sensors, to provide additional more accurate spatial resolution (i.e. more precise surgical guidance) while maintaining or increasing probe sensitivity.

In the case of solid state probes, each sub-element is read separately by multi-channel readout electronics placed in probe 12. In the case of scintillation probes, multi-element photo-detectors are used either incorporated in probe 12, or placed at the end of multi-fiber light guide in optical contact with probe 12.

The gamma radiation sensor 34 in probe 12 can be made of, for example: a solid state material, such as CdZnTe, CdTe, etc, or a scintillator material such as high stopping power crystal scintillators (BGO, LSO, LYSO, GSO, LGSO, etc). The additional positron sensitive material can be also made of a thin solid state material such as silicon, or a thin bright scintillator such as plastic scintillator, CsI(Tl), CaF (Eu), YAP, YAG, CsF, etc.

Scintillation light from the scintillator sensor can be detected by a directly coupled or via a light guide coupled photosensor. Several types of photodetectors can be used: photomultipliers, silicon photodiodes, avalanche photodiodes, silicon photomultipliers, and hybrid photomultipliers (with silicon element)

Two major variants or configurations of the system can be utilized: a flexible version when used during biopsy or surgery primarily involving organs such as breast, head, neck, extremities, in this case a smaller and also compact coincidence imager is used attached to, for example, an articulated arm for easy manipulation around the organ(s) in the surgery field; and a more static version with a larger field of view coincidence imager 14, for example, placed under or directly embedded in the patient bed 13 (see FIG. 1). The more fixed position of imager 14 in this implementation as compared to the flexible version, can offer more accurate and stable position calibration for more precise guidance information about uptake region(s) position and extent.

During surgery the feedback information provided to the probe operator/surgeon has to be prompt, provided with minimal delay. Therefore, while the in-depth analysis of the collected and/or available data from the probe and coincident imager 14 is important, fast feedback to the operator/surgeon is of prime value.

Different aspects of the formed coincident image in coincidence imager 14 can be used to provide precise information to the probe operator as to the existence and position of the uptake region (lesion etc): average position (center of gravity of the count distribution); size and shape of the projected distribution, providing information about the extent and size of the uptake, for example isolated hot spots vs larger area/volume; information about the depth of the uptake (in the case of simpler point-like uptake regions).

In the special implementation of the concept for prostate cancer depicted in FIG. 6, a small coincidence imager 14A can be trans-rectally inserted into the patient and placed behind or under the prostate 15 to provide high sensitivity and high spatial resolution in mapping prostate cancer tissue and specifically assist in defining cancer margins and any residual cancer tissue during and after a surgical procedure. The function of such an arrangement is two-fold: guide the surgeon before and during cancer surgery, and provide feedback if the cancerous tissue is entirely removed while assuring minimal damage to healthy surrounding tissue. Through the proximity of both detectors to the organ, the detection sensitivity is highly maximized. The trans-rectal probe can be either simple non-imaging or an imaging device composed of an array of small sensor elements to provide better spatial resolution and sensitivity. An example of such a sensor array is a pixellated LYSO/LSO/GSO phoswich structure of 2×2×2 mm pixels optically coupled to position sensitive photodetector via a fiberoptic lightguide.

EXAMPLES

Example 1

Figure 7:
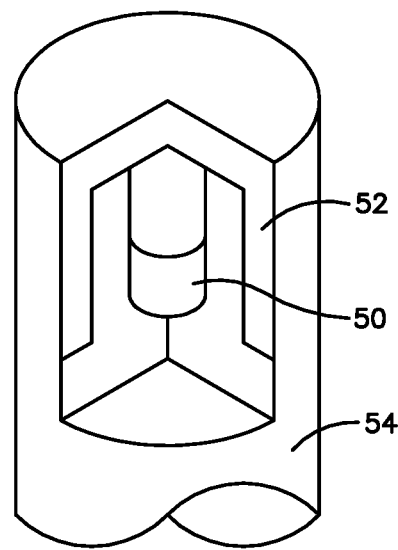
FIG. 7 a partially cutaway view of one embodiment of the probe portion of the surgical guidance system of the present invention.

A probe comprising an about 1 cm cube LSO crystal attached to a 1.4 cm diameter R647 Hamamatsu PMT; and an imaging detector comprising a 20×15 cm LYSO array of 2×2×15 mm LYSO pixels (pitch 2.1 mm) optically attached to a 4×3 array of Hamamatsu flat panel H8500 PSPMTs is used to image a "point" microCi: Na22 source 50 embedded in acrylic 52 representing a lesion in a housing 54 (see FIG. 7).

Geometry:
In this example, the "lesion" is about 2 cm from the probe sensor center. The lesion-to-imaging detector distance is about 13 cm.

Example 2

A smaller probe comprising a 3×3×10 mm BGO crystal is attached to a R1635 Hamamatsu PMT. Count rate curves are measured while moving (scanning) the probe close to the source. Both single mode and coincidence mode are used. The results of using these two systems are shown in Table 1.

TABLE 1

| Position (mm) | Single Rate (Hz) | Coinc. Rate (Hz) | Image ROI (2 min counts) |
| --- | --- | --- | --- |
| 0 | 1310 | 665 | 1633 |
| 2.5 | 1650 | 815 | 1625 |
| 5.0 | 1990 | 985 | 3255 |
| 7.5 | 2295 | 1120 | 4079 |
| 10 | 2380 | 1125 | 2496 |
| 12.5 | 2220 | 1065 | 1859 |
| 15 | 1840 | 875 | 1795 |
| 17.5 | 1530 | 620 | |
| Random | | | 1400 |

Figure 8:
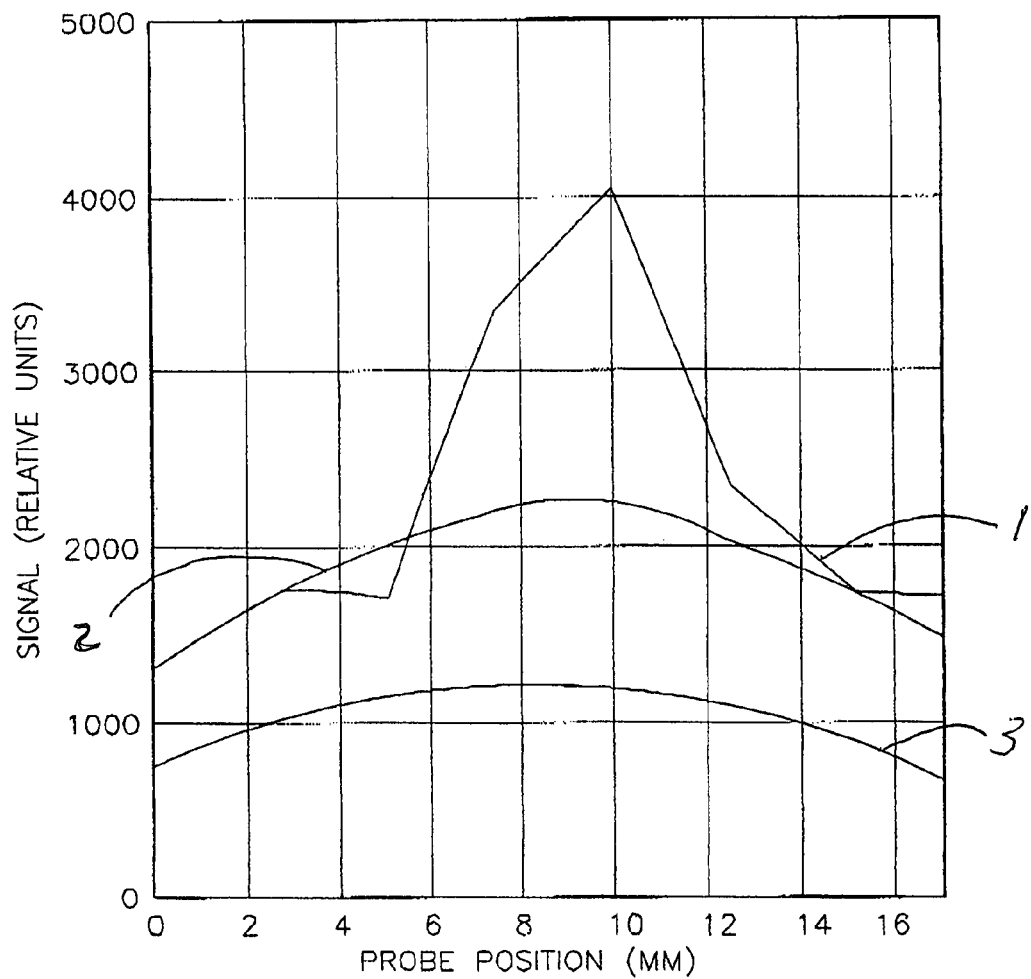
FIG. 8 is a graph showing the results of a test performed to compare the accuracy of the device of the present invention with single element hand-held probes.

The above data are represented graphically in FIG. 8. Curve 3 shows signal in coincidence with the full detector. Curve 2 shows the singles (non-coincidence) rate result. Curve 1 depicts the results using coincidence with a selected ROI sector in the imaging detector.

The observed sharper position definition is due to a coincidence effect between the probe and the region in the imager. This demonstrates much better guidance capabilities of the system, as compared to a simple gamma/beta probe.

As the invention has been described, it will be apparent to those skilled in the art that the same may be varied in many ways without departing from the spirit and scope of the invention. Any and all such modifications are intended to be included within the scope of the appended claims.

What is claimed is:

1. A surgical guidance system for detecting areas of increased uptake of biomarker within a region of interest (ROI) on a patient treated with a beta-emitting bio-marker comprising:
  a) a hand-held detection probe including
    1) a first scintillator layer for converting incident beta radiation to light, said first scintillator layer producing a first pulse shape;
    2) a second scintillator layer for converting incident beta radiation to light, said second scintillator layer in optical contact with said first scintillator layer and producing a second pulse shape;
    3) a gamma scintillator layer in optical contact with said second scintillator layer to detect one of a pair of 511 keV annihilation gamma rays from said ROI and producing a third pulse shape; and
    4) a photodetector in optical contact with said gamma scintillator layer;
  b) a coincidence detector for detecting gamma rays from the ROI, said coincidence detector including a second gamma scintillator layer to detect the other of the pair of 511 keV annihilation gamma rays from said ROI and producing a fourth pulse shape;
  c) a hardware processor for separating the pulse shapes on the basis of their different time decay and amplitude characteristics; and
  d) a coincidence imager for displaying a formed coincident image of the ROI from the pulse shapes of the hand-held detection probe and the coincidence detector, said surgical guidance system producing an intensified image at said areas of increased uptake of biomarker.

2. The surgical guidance system of claim 1 wherein said first scintillator layer is selected from the group consisting of plastic scintillator, YAP crystal scintillator, and CaF(Eu) scintillator material.

3. The surgical guidance system of claim 1 wherein said second scintillator layer is selected from the group consisting of silicon, CsI(Tl), CaF(EU), YAG, and CsF.

4. The surgical guidance system of claim 1 wherein said gamma scintillator layer of said hand-held probe is selected from the group consisting of BGO, LSO, LYSO, GSO, and LGSO.

* * * * *